United States Patent [19]
Johnson

[11] Patent Number: 6,031,567
[45] Date of Patent: Feb. 29, 2000

[54] METHOD AND APPARATUS FOR VIDEO LUMBER GRADING

[75] Inventor: Emeric Johnson, Salmon Arm, Canada

[73] Assignee: CAE Electronics Ltd. CAE Electronique Ltee, St. Laurent, Canada

[21] Appl. No.: 08/841,628

[22] Filed: Apr. 30, 1997

Related U.S. Application Data

[60] Provisional application No. 60/016,606, May 1, 1996.

[51] Int. Cl.⁷ ...................................................... H04N 7/18
[52] U.S. Cl. ............................................. 348/91; 348/130
[58] Field of Search ................................. 348/89, 91, 86, 348/87, 88, 92, 93, 94, 95, 130; H04N 7/18

[56] References Cited

U.S. PATENT DOCUMENTS

| | | | |
|---|---|---|---|
| 4,724,482 | 2/1988 | Duvent | 348/164 |
| 4,827,142 | 5/1989 | Hatje | 250/559.25 |
| 4,992,949 | 2/1991 | Arden | 354/478.11 |
| 5,257,101 | 10/1993 | Lee | 348/95 |
| 5,307,294 | 4/1994 | Aman et al. | 702/128 |
| 5,357,112 | 10/1994 | Steele et al. | 250/340 |
| 5,519,793 | 5/1996 | Grannes | 382/266 |

*Primary Examiner*—Tommy P. Chin
*Assistant Examiner*—Luanne P. Din
*Attorney, Agent, or Firm*—Antony C. Edwards

[57] ABSTRACT

A lumber video grading apparatus includes a vision system, processors, a grading station having visual displays, a storage and retrieval device, an identification device, and a timing system. The vision system may include cameras mounted proximate to a lumber transfer for optically acquiring real time images of exposed cut surfaces of lumber pieces conveyed on the lumber transfer. The processors process the real time images into individually identifiable retrievably storable images and also into visually displayable real time images. A selectable lumber grade is correlated at a grading station to selectable pieces of lumber on the lumber transfer. The displayable real time images or later retrieved individually identifiable retrievably storable images are displayable on a visual display at the grading station. The individually identifiable retrievably storable images are retrievably storable on, and selectively retrievably from, the storage and retrieval device. The identification device is for selectively applying an individual identifier to the selectable pieces of lumber on the lumber transfer. The timing system is for correlating the real time images to the selectable lumber pieces.

16 Claims, 2 Drawing Sheets

METHOD AND APPARATUS FOR VIDEO LUMBER GRADING

This APPLN claims benefit of Provisional APPLN No. 60/016,606 May 1, 1996.

FIELD OF THE INVENTION

This invention relates to a method and apparatus for grading lumber, and in particular relates to a video sawmill lumber grading system.

BACKGROUND OF THE INVENTION

The conventional way to grade lumber is to have personnel called graders manually grade the lumber, ie. to have the lumber pass by graders on a transfer (moving chains), and have the graders pick up and turn by hand individual boards, visually inspect them and assign a grade by a mark on the board, and potentially to assign a trimmer solution. Improved methods can feature automatic board turners, pushing buttons to enter the grade or the like.

It is known in the art that trimmer and edger solutions may be obtained by using optimizers. Optimizers may manually position the lumber before preset saws or manipulate laser lines or the like to define where a desired saw cut should be and have positioning equipment move the lumber and saws accordingly.

It is an object of the invention to provide an improved view or image of sawn boards to increase grading accuracy and productivity.

It is also an object of the invention, that, by providing superimposed adjustable images on to a video monitor, the grader may more easily and more accurately add cutting solutions and grade decisions to the board when grading, to further enhance productivity.

It is further an object of the invention that, by having graders viewing images rather than having to physically turn the boards, repetitive motion type injury compensation claims will be reduced.

SUMMARY OF THE INVENTION

The method and apparatus for video lumber grading of the present invention captures video images of lumber, whether boards or flitches, and presents these images and/or electronically enhanced images to workers who assign grades and/or cutting solutions to the lumber that will be used in downstream machinery to achieve desired production and/or optimizing results.

The video images, along with any worker inputs, may be stored on a storage medium, whether on tape, disc, analog or digital, etc., for future use, for example, by lumber inspectors or purchasers. The stored images may be cross-referenced to the actual lumber or eventual lumber package by way of marking of the lumber or lumber package with an identifying mark, such as a unique bar code, which would allow retrieval of the video images of the lumber. The lumber images may be sent in real time or via a storage medium to customers or other end users who may view the actual image of the lumber, or of all the boards in the lumber package, so that the end users may, for example, make an informed offer to purchase that lumber.

Thus, a sawmill may have a package of lumber, with each board within the package identified by its own bar code, where the bar code uniquely refers to a stored video image of the lumber. The lumber package may be stored and only a copy of the video sent to the end users where graders or buyers may view the video of the lumber pieces in the lumber package piece by piece and submit a bid for the package or individual pieces. The end users may then re-sell the lumber based on the video images before taking delivery. The delivered lumber may be checked against the stored video images at any time, in that the boards retain their bar code identifiers. Also, the stored video images may contain the electronically enhanced features and reference lines (as hereinafter described) to assist viewers to evaluate the lumber at a later time and place.

In a mechanical implementation of the present invention, mechanical lumber handling transfers of a known kind singulate boards and move the singulated boards so they arrive in a consistent orientation over a position where a video camera acquires their image. The singulated boards are then transferred downstream to other sawmill equipment. An image acquisition system, consisting of cameras (preferably digital), lighting, a means for timing the acquisition of the image with the moving board and a video recorder store the images. The cameras may be located above the board pathway, such as a chainway, and below the pathway if a board turner is not used. The cameras are positioned to allow lumber graders to view all sides of a board in real time motion pictures, or in still pictures, on a video screen monitor in a manner that gives the graders a better or enhanced view than may be conventionally achieved in the lumber grading process used in the industry today. Movable reference lines may be imposed on the monitor. The operator or grader may position the reference lines over the board image to provide additional information such as edging solutions or trimming solutions. A data recorder stores the chain lug position corresponding to the lumber position, and this information is relayed to a data processor. The data processor processes and correlates the information.

When the cameras are used below the chain runs, the chain runs are sectioned, and thin rods or the like create a link, that is, a transit medium through which the boards may be viewed, between the aligned chain run sections so as to provide an unobstructed view from below and to provide a surface for the boards to move onto and over as the lower cameras captured the boards image. A board pusher pushes the board between the split chain runs, allowing a clear image to be obtained by the lower cameras. This procedure may provide a pause so as to present a better view of the board momentarily. Single cameras may be positioned in the middle of the board using multiple focus point lenses. Alternatively, multiple cameras having optimized lighting are provided, depending on the maximum length of the boards being graded. This system captures better images of the boards than is available to the naked eye in today's lumber grading environment. Multiple images of the same board may be merged into one image and placed onto the video screen further enhancing the view of each board, so as to result in better grading than possible today. Grader video stations may be located adjacent to the grade transfer so the grader may identify the actual board shown on the video image and physically check it if desired.

A computer assembles the images for the video terminal from the images acquired from the acquisition system and manipulates them according to the requirements discussed below. The computer also controls the buffer and distributes images to the graders as required and assigns a bar code or other identification to the board. The bar code is automatically printed by inkjet or other means onto the board after viewing so as to cross reference the board to the video image. The computer directs the images as required so they may be dealt to the next available grader or worker. A buffer may hold the images in memory and distribute them to the graders as needed. This may allow the operator to view the board for a longer period of time if needed. A high resolution video recorder stores the images, or manipulated images, with their related bar code information. The images (or manipulated images) are sent to a video terminal to be viewed by a grader. The grader may enter data relating to these images, such as grade, at an input station or the grader may be able to manipulate superimposed lines etc. on the video monitor so as to make a cutting decision and assign the cutting solution on the board and have that cutting solution effected by downstream equipment or attached to the stored video image.

Software to enhance the image or assist the operator to make decisions may be incorporated. The software may: provide enhancement on the video screen of actual defects on the board; provide references to assist the graders in establishing the size of a defect (i.e. overlay all knots with circles giving knot diameter); detect wane by detecting the difference in light reflected by the smooth flat plane surfaces of the top and edge of the board, and the curved or irregular wane surface; provide references on the video screen such as lines and text indicating various lengths, widths and thickness'; provide other references such as colour codes to compare the actual board to certain shades as required; provide reference lines on the monitor that the operator can position over the board to provide additional information such as edging solutions or trimming solutions; have the software suggest a grade or cut solution then allow the operator to optimize it; provide a value of the board or the cutting solutions of that board with data inputted by the grader and based on tables or data within the software; assist in the training of the workers by allowing multiple decisions to be made in real time or with stored images, and allowing these decisions to be compared, (i.e. trainee vs trainer and results tabulated and reported); provide the option of zooming in to specific areas of the board to examine more closely areas of interest; allow the boards to be held in an electronic buffer and "dealt" to the lumber graders as they are ready for them, for example, difficult boards could have more time spent on them and easier boards processed more quickly, so that through-put would then be based on the average of the graders, not the slowest one; and, grades or cut decisions could be assigned to the board by lug spaces or an assigned number and then passed onto a programmable logic controller (PLC) for use downstream.

In addition to the above, boards could be identified and their video image stored without being graded if the sale of the board was not affected by being un-graded.

Production runs could be stored on the video tape or other mass storage retrievable medium. Graders decisions could be checked at some time in the future to check the accuracy of the graders.

The boards could be re-graded against a different set of grade rules using the video images and a new grade assigned against the bar code for each piece of lumber at some time in the future.

This system would lend itself to complete automatic grading as the development of imaging software improves, that is, the computer could be trained to recognize defects that are present in boards, thus eventually relieving the operator entirely, from a job that is probably the most monotonous job in the sawmill.

In summary, the lumber video grading apparatus of the present invention includes vision means, means for data processing, a grading station having visual displays, storage and retrieval means, identification means, and timing means. The vision means is mounted proximate to a lumber transfer means for optically acquiring real time images of exposed cut surfaces of lumber pieces conveyed on the lumber transfer means. The means for processing is for processing the real time images into individually identifiable retrievably storable images and also into visually displayable real time images. The grading station includes means for selectively correlating a selectable lumber grade to selectable pieces of lumber on the lumber transfer means. The displayable real time images or later retrieved individually identifiable retrievably storable images are displayable on a visual display at the grading station. The individually identifiable retrievably storable images are retrievably storable on, and selectively retrievably from, a storage and retrieval means. The identification means is for selectively applying an individual identifier to the selectable pieces of lumber on the lumber transfer means. The timing means is for correlating the real time images to the selectable lumber pieces.

The method of lumber grading of the present invention includes the steps of: (a) optically acquiring real time images of exposed cut surfaces of lumber pieces conveyed on a lumber transfer means by means of vision means mounted proximate to said lumber transfer means, (b) processing, by processing means, said real time images into individually identifiable retrievably storable images and into visually displayable real time images, (c) retrievably storing said individually identifiable retrievably storable images on, so as to be selectively retrievable from, a storage and retrieval means for retrievably storing said individually identifiable retrievably storable images, (d) displaying said real time images and selectively correlating at a grading station, by correlating means, a selectable lumber grade to selectable pieces of lumber of said pieces of lumber on said lumber transfer means, wherein said grading station includes a visual display for selective displaying of said visually displayable real time images or said individually identifiable retrievably storable images, (e) selectively applying an individual identifier, by identification means, to said selectable lumber pieces of said lumber pieces on said lumber transfer means, and, (f) correlating said real time images, by timing means, to said selectable lumber pieces.

Advantageously, the means for processing further includes means for queuing and distributing the individually identifiable retrievable storable images between a plurality of grading stations according to the availability of the grading stations.

In a further aspect, the means for processing further includes buffer means for increasing a display time on the visual display at a grading station of the real time images corresponding to the selectable pieces of lumber requiring scrutiny by an operator for a longer period of time. The means for processing also includes means for decreasing the display of selectable pieces of lumber to those which only require scrutiny by an operator for a shorter period of time.

In a further aspect, the means for processing further includes means for overlaying onto the real time images means for selectively optimizing cutting solutions for the selectable lumber pieces for display on the visual display.

Further advantageously, the lumber grading apparatus, and corresponding method of the present invention includes correlation means for correlating the individually identifiable retrievably storable images stored on the storage and retrieval means with the identification means, whereby the stored images may be later retrieved and the selectable lumber pieces corresponding to the stored images may be graded or otherwise assessed.

BRIEF DESCRIPTION OF THE DRAWINGS

The invention will be better understood by reference to drawings, wherein.

DETAILED DESCRIPTION OF THE PREFERRED EMBODIMENT

Figure 1:
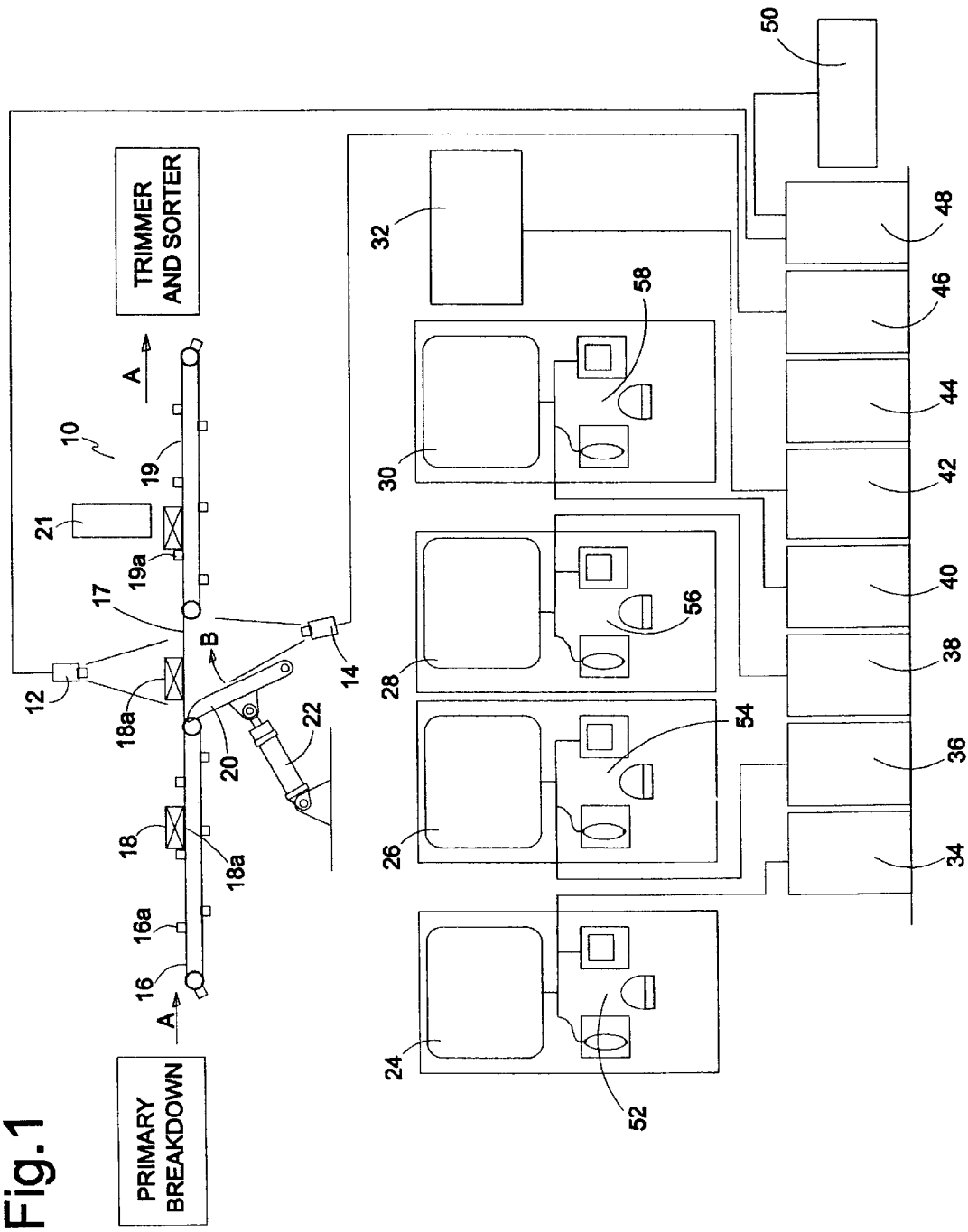
FIG. 1 is a side elevation view according to a preferred embodiment of the invention, with a block diagram showing the relationship of the electronic devices.

Referring to the drawing figures wherein similar characters of reference represent corresponding parts in each view, the apparatus is generally indicated by the reference numeral 10.

As best seen in FIG. 1, cameras 12 and 14 are positioned in generally opposed facing relation vertically above and below, respectively, chain run 16. Chain run 16 includes chain lugs 16a which are evenly spaced apart and move with the chains on chain run 16. The chain lugs 16a move the boards 18 along in an evenly spaced continuous flow in direction A. Thin rods 17 or the like allow the underside 18a of board 18 to be clearly seen from the bottom by camera 14. A board pusher 20 is actuated in direction B by a cylinder 22. The board pusher 20, which may be below or above the travel path, pushes board 18 across thin rods 17 where the board is picked up by chain lugs 19a on a downstream chain run, where board 18 is marked by conventional board marker 21 or other machinery for affixing bar code identifiers or the like. Board 18 then moves downstream on to a trimmer (not shown) and continues on to a sorter (also not shown).

Video monitor stations 24, 26, 28 and 30 include grader consoles 52, 54, 56 and 58. Also shown are the computer components necessary, including video drivers 34, 36, 38 and 40. Also included is processor 42, memory board 44, frame grabbers (one for each camera), 46 and 48 and a video recorder 50 for storing the images. Programmable logic controller (PLC) 32 allocates instructions for each board 18 as has been entered by the operator, to the board marker 21, the trimmer (not shown) and the sorter (not shown).

Figure 2:
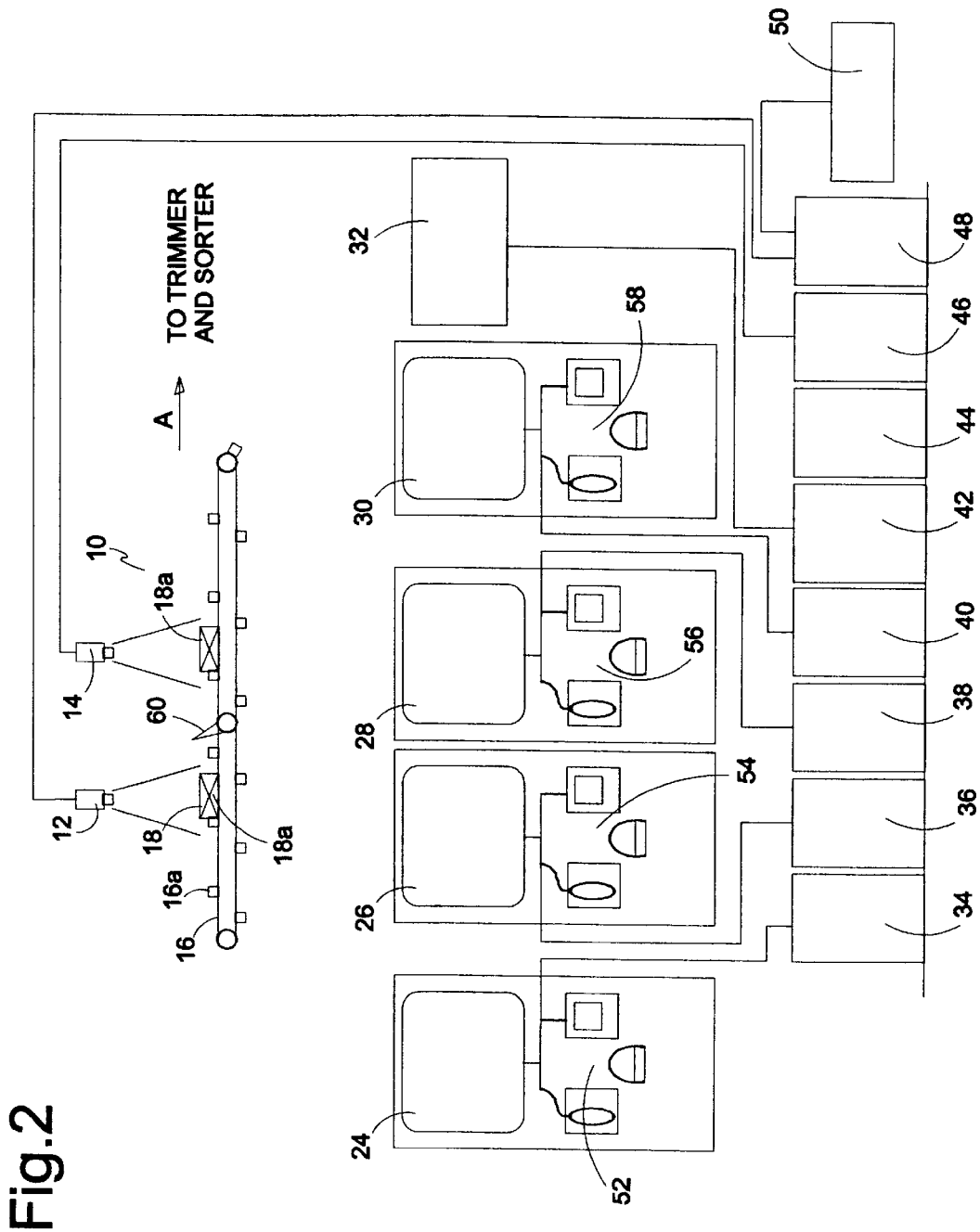
FIG. 2 is a side elevation view according to an alternate preferred embodiment of the invention, with a block diagram showing the relationship of the electronic devices.

As seen in FIG. 2, an alternative system has cameras, 12 and 14 both above chain runs 16. This embodiment accommodates a board turner 60, which flips the board 180 degrees about a longitudinal board axis for viewing the underside 18a of each board 18.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A video assisted lumber grader for video scanning, grading, and cataloguing of sawn lumber after primary breakdown of the lumber comprising:

vision means mounted downstream of primary log breakdown and proximate to a lumber transfer means, said vision means for optically acquiring real time images of exposed cut surfaces of individual sawn boards conveyed on said lumber transfer means, a grading station comprising means for correlating a lumber grade to said sawn boards on said lumber transfer means, said grading station further comprising a visual display for displaying of said real time images, identification means for selectively applying an individual identifier to said sawn boards on said lumber transfer means, timing means for correlating said real time images to said sawn boards wherein said real time images facilitate informed grading or purchasing decisions for each of said sawn boards, means for processing said real time images into storable images and into visually displayable images, said visual display for selective displaying of said visually displayable images or said storable images, said storable images retrievably storable on, and selectively retrievable from, a storage and retrieval means, and correlation means for correlating said storable images stored in said storage and retrieval means with said identification means wherein said stored images may be later retrieved and said sawn boards corresponding to said stored images graded or otherwise assessed.

2. The video assisted lumber grader of claim 1, wherein said means for processing further comprises means for queuing and distributing said storable images between a plurality of said grading stations according to availability of said grading stations.

3. The video assisted lumber grader of claim 1 wherein said means for processing further comprises buffer means for increasing a display time on said visual display of said real time images requiring scrutiny by an operator for a longer period of time, and means for decreasing said display time sawn boards requiring scrutiny by said operator for a shorter period of time.

4. The video assisted lumber grader of claim 1 wherein said means for processing further comprises means for overlaying onto said real time images means for optimizing cutting solutions for said sawn boards for display on said visual display.

5. The video assisted lumber grader of claim 2 wherein said means for processing further comprises means for overlaying onto said real times images means for optimizing cutting solutions for said sawn boards for display on said visual display.

6. The video assisted lumber grader of claim 2 further comprising correlation means for correlating said storable images stored in said storage and retrieval means with said identification means whereby said stored images may be later retrieved and said sawn boards corresponding to said stored images graded or otherwise assessed.

7. The video assisted lumber grader of claim 3 further comprising correlation means for correlating said storable images stored in said storage and retrieval means with said identification means whereby said stored images may be later retrieved and said sawn boards corresponding to said stored images graded or otherwise assessed.

8. The video assisted lumber grader of claim 4 further comprising correlation means for correlating storable images stored in said storage and retrieval means with said identification means whereby said stored images may be later retrieved and said sawn boards corresponding to said stored images graded or otherwise assessed.

9. A method of video assisted lumber grading for video scanning, grading, and cataloguing of sawn lumber after primary breakdown of the lumber comprising the steps of:

(a) optically acquiring real time images of exposed cut surfaces of each board of a plurality of sawn lumber pieces conveyed on a lumber transfer means by means of vision means mounted downstream of primary breakdown and proximate to said lumber transfer means, (b) displaying said real time images and correlating at a grading station, by correlating means, a lumber grade to of said sawn lumber pieces on said lumber transfer means, wherein said grading station includes a visual display for displaying of said real time images, (c) applying an individual identifier, by identification means, to said boards of said lumber pieces on said lumber transfer means, (d) correlating said real time images, by timing means, to said boards so as to facilitate informed grading or purchasing decisions for each of said boards, (e) processing, by processing means, said real time images into storable images and into real time images, (f) retrievably storing said storable images on, so as to be selectively retrievable from, a storage and retrieval means, (g) displaying of either said real time images for grading of said boards or, from said storage and retrieval means, said storable images for grading or purchasing of said boards, and (h) correlating by correlation means for correlating said storable images stored in said storage and retrieval means with said identification means wherein said stored images may be later retrieved and said boards corresponding to said stored images graded or otherwise assessed.

10. The method of video assisted lumber grading of claim 9, wherein said means for processing further comprises means for queuing and distributing said storable images between a plurality of said grading stations according to availability of said grading stations.

11. The method of video assisted lumber grading of claim 9 wherein said means for processing further comprises buffer means for increasing a display time on said visual display of said real time images requiring scrutiny by an operator for a longer period of time, and means for decreasing said display time for said boards requiring scrutiny by said operator for a shorter period of time.

12. The method of video assisted lumber grading of claim 9 wherein said means for processing further comprises means for overlaying onto said real time images means for optimizing cutting solutions for said boards for display on said visual display.

13. The method of video assisted lumber grading of claim 10 wherein said means for processing further comprises means for overlaying onto said real time images means for optimizing cutting solutions for said for display on said visual display.

14. The method of video assisted lumber grading of claim 10 further comprising correlation means for correlating said storable images stored in said storage and retrieval means with said identification means wherein said stored images may be later retrieved and said corresponding to said stored images graded or otherwise assessed.

15. The method of video assisted lumber grading of claim 11 further comprising correlation means for correlating said storable images stored in said storage and retrieval means with said identification means wherein said stored images may be later retrieved and said boards corresponding to said stored images graded or otherwise assessed.

16. The method of video assisted lumber grading of claim 12 further comprising correlation means for correlating said storable images stored in said storage and retrieval means with said identification means wherein said stored images may be later retrieved and said boards corresponding to said stored images graded or otherwise assessed.

\* \* \* \* \*